United States Patent [19]

Mar

[11] 4,273,558

[45] Jun. 16, 1981

[54] DETERMINATION OF TOTAL ORGANIC CARBON IN AN AQUEOUS SAMPLE CONTAINING HALIDE ION

[75] Inventor: Danny M. Mar, Daly City, Calif.

[73] Assignee: Envirotech Corporation, Menlo Park, Calif.

[21] Appl. No.: 128,066

[22] Filed: Mar. 7, 1980

[51] Int. Cl.³ .............................................. G01N 33/18
[52] U.S. Cl. .................................. 23/230 PC; 23/906; 252/408; 422/79; 422/81
[58] Field of Search ............ 23/230 PC, 906; 422/79, 422/81; 252/408

[56] References Cited

U.S. PATENT DOCUMENTS

| | | | |
|---|---|---|---|
| 3,784,359 | 1/1974 | Parth | 422/79 |
| 3,854,881 | 12/1974 | Cohen | 422/79 |
| 3,955,924 | 5/1976 | Northmore et al. | 422/79 X |
| 4,217,108 | 8/1980 | Melzer | 23/906 |

OTHER PUBLICATIONS

Ehrhardt, "A New Method for the Automatic Measurement of Dissolved Organic Carbon in Sea Water," *Deep-Sea Research*, vol. 16, pp. 393–397 (1969).

"Ein neues Verfahren zur Bestimmung von Organisch gebundenem Kohlenstoff in wasserdurch photochemisch Oxidation," Von Wasser, vol. 43, pp. 315–325 (1974).

*Primary Examiner*—Ronald Serwin
*Attorney, Agent, or Firm*—Robert E. Krebs; Thomas J. McNaughton; Thomas S. MacDonald

[57] ABSTRACT

Total organic carbon in an aqueous sample containing halide ion is determined by preparing an aqueous solution containing an oxidizing agent and mercuric monohalide ion without forming an insoluble precipitate, introducing the sample into the solution so formed, irradiating the solution and sample with ultraviolet energy to oxidize organic matter in the sample to produce carbon dioxide, sparging the carbon dioxide so produced from the solution, and measuring total carbon in the carbon dioxide. The aqueous solution is prepared by mixing the oxidizing agent with a solution containing mercuric monohalide ion, which is formed by adding a quantity of mercuric halide and a quantity of mercuric nitrate to an aqueous solution containing nitric acid, where the molar concentration of the mercuric halide is at least equal to the molar concentration of the mercuric nitrate.

27 Claims, No Drawings

DETERMINATION OF TOTAL ORGANIC CARBON IN AN AQUEOUS SAMPLE CONTAINING HALIDE ION

BACKGROUND OF THE INVENTION

1. Field of the Invention

This invention pertains to the determination of total organic carbon in an aqueous sample containing halide ion, e.g., seawater.

2. State of the Prior Art

A technique for determining total organic carbon (TOC) in a seawater sample was described in an article by M. Erhardt entitled "A New Method for the Automatic Measurement of Dissolved Organic Carbon in Sea Water" published in *Deep-Sea Research,* Vol. 16, pages 393–397 (1969), in which dissolved organic matter in the sample is oxidized with a persulfate oxidizing agent using ultraviolet radiation to promote the oxidation, and in which carbon dioxide formed by oxidation of the organic matter is quantitatively detected to determine total carbon.

TOC in an aqueous sample containing dissolved organic matter has been determined by irradiating the sample with ultraviolet radiation from a low-pressure mercury vapor lamp immersed in the sample in order to oxidize the organic matter to carbon dioxide, sparging the carbon dioxide so produced from the reactor, and then measuring total carbon in the sparged carbon dioxide. Such a technique was described in an article by P. Wölfel and H. Sontheimer entitled "Ein neues Verfahren zur Bestimmung von organisch gebundenem Kohlenstoff im Wasser durch photochemische Oxidation" published in *Vom Wasser,* Vol. 43, pages 315–325 (1974).

In co-pending U.S. patent application Ser. No. 127,333, a technique was described for determining total carbon in each one of a plurality of liquid samples by maintaining a continuous flow of a liquid containing an oxidizing agent (e.g., persulfate ion $S_2O_8^{--}$ or hydroxy free radical .OH) through a reactor into which the samples are introduced in succession, and by irradiating each sample in the reactor with ultraviolet radiation from a mercury vapor lamp immersed in the sample to oxidize carbonaceous matter in the sample and thereby produce carbon dioxide that can be measured for total carbon.

In chemical oxygen demand (COD) analysis, where dichromate ion is used as the oxidizing agent, free chloride ion $Cl^-$ in a sample would react with the oxidizing agent, thereby decreasing the amount of oxidizing agent available for the analysis. It was known, however, that by adding mercuric sulfate $HgSO_4$ to the sample, free $Cl^-$ would be complexed with $Hg^{++}$ to form mercuric chloride $HgCl_2$, thereby removing free $Cl^-$ from interfering with the analysis. However, adding $HgSO_4$ to an aqueous sample containing persulfate ion $S_2O_8^{--}$ produces an insoluble precipitate, i.e., mercuric oxide $HgO$, which cannot react with chloride ion $Cl^-$.

It was known that mercuric monochloride ion $HgCl^+$ can be formed by mixing equal molar concentrations of mercuric chloride $HgCl_2$ and mercuric nitrate $Hg(NO_3)_2$ together in aqueous solution. However, $HgCl^+$ is not usually used to complex free chloride ion $Cl^-$ for analytical purposes. Use of a solution containing $HgCl^+$ for complexing free chloride ion $Cl^-$ appears to have had no practical application until the present invention.

OBJECTS OF THE INVENTION

It is an object of the present invention to provide a technique for determining total organic carbon in an aqueous sample containing halide ion using a reagent that oxidizes organic matter in the sample in the presence of ultraviolet radiation, where the rate of oxidation of the organic matter is not significantly suppressed due to halide ion interference.

It is a particular object of the present invention to provide a technique for determining total organic carbon in an aqueous sample containing halide ion by ultraviolet-promoted oxidation of organic matter in the sample using persulfate ion as an oxidizing agent, where suppression of the rate of oxidation of the organic matter due to halide ion interference is minimal.

More specifically, it is an object of the present invention to provide a reagent for use in oxidizing organic matter in an aqueous sample containing halide ion in the presence of ultraviolet radiation, where the reagent contains persulfate ion and mercuric monochloride ion.

It is likewise an object of the present invention to provide a precipitate-free reagent containing persulfate ion and mercuric monochloride ion for use in ultraviolet-promoted oxidation of organic matter in an aqueous sample containing halide ion.

DESCRIPTION OF PREFERRED EMBODIMENT

Total organic carbon (TOC) in an aqueous sample can be determined by a process that includes the steps of oxidizing the organic matter in the sample to carbon dioxide $CO_2$ in a reactor using an oxidizing agent and ultraviolet radiation, sparging the $CO_2$ so produced from the reactor, and then measuring total carbon in the sparged $CO_2$. The reactor could be a vessel that is filled to a desired level with a liquid containing the oxidizing agent and the sample, as described in the Wölfel and Sontheimer article, op. cit.; or the reactor could be configured as a coil through which a liquid containing the oxidizing agent and the sample passes around the envelope of an elongate mercury vapor lamp, as described in the article by Erhardt, op. cit. The configuration of the reactor is not essential to the present invention. Total carbon in the sparged $CO_2$ can be measured conventionally by coulometric titration, non-dispersive infrared detection means, or conductometric means. Alternatively, the $CO_2$ sparged from the reactor could be converted to methane $CH_4$, which can be quantitatively detected by a flame ionization detector.

According to a technique described in the aforementioned co-pending U.S. patent application Ser. No. 127,333 for determining total carbon in a plurality of aqueous samples, a continuous flow of a liquid containing an oxidizing agent (e.g., persulfate ion $S_2O_8^{--}$ or hydroxy free radial .OH) is passed through a reactor in which a mercury vapor lamp is positioned, and the samples are introduced in succession into the reactor. Typically, a 0.6 milliliter per minute flow of a 2% concentration aqueous solution of potassium persulfate $K_2S_2O_8$, sodium persulfate $Na_2S_2O_8$ or ammonium persulfate $(NH_4)_2S_2O_8$ into a 100 milliliter reactor is used. The mercury vapor lamp is immersed in the aqueous solution in the reactor, and emits radiation particularly at the 2537 angstrom wavelength in the ultraviolet region of the spectrum and the 1849 angstrom wavelength in the so-called vacuum-ultraviolet region. The radiation causes oxidation of carbonaceous matter in each sample. $CO_2$ produced by oxidation of the carbonaceous matter is sparged from the aqueous solution in the reactor by conventional means, and total carbon in the sparged $CO_2$ is measured by conventional means.

When an aqueous sample to be analyzed for TOC contains halide ion, as in the case of seawater or a solution containing a mineral acid such as hydrogen chloride HCl, the halide ion absorbs ultraviolet radiation below 2000 angstroms and thereby suppresses the rate at which oxidation of organic matter in the sample can occur. For a typical seawater sample introduced into a reactor holding 100 milliliters of 2% $S_2O_8^{--}$ ion, the time required to oxidize organic matter in the sample with ultraviolet radiation from a mercury vapor lamp is on the order of eight minutes or longer. The TOC analysis of such a sample typically takes the form of a graphic time-varying signal indicating the amount of $CO_2$ sparged from the reactor. Total carbon in the sample is measured by integrating the $CO_2$ detection signal over the time interval required for complete oxidation of the organic matter in the sample. When the time interval required to oxidize the organic matter in the sample is as long as eight minutes, precision in the measurement suffers due to "tailing" of the signal.

The present invention can be practiced using techniques developed in the prior art for oxidizing carbonaceous matter in an aqueous sample to carbon dioxide by means of an oxidizing agent and ultraviolet radiation, and for measuring total carbon in the carbon dioxide so produced. The present invention is an improvement over the prior art techniques, however, in enabling an aqueous sample containing halide ion to be oxidized in much shorter time than was possible in the prior art. The present invention therefore makes possible greater precision in TOC analysis of an aqueous sample containing halide ion, in a shorter analysis time, than was possible in the prior art.

In accordance with the present invention, an aqueous sample containing halide ion is analyzed for TOC by being introduced into an aqueous solution in which an oxidizing agent and mercuric monohalide ion are present without forming an insoluble precipitate; and the solution is irradiated with ultraviolet radiation to promote oxidation of organic matter in the sample. The mercuric monohalide ion forms a complex with the halide ion, thereby effectively removing from the solution the halide ion that would otherwise have interfered with the TOC analysis.

It is a feature of the present invention that use of mercuric monohalide ion does not form an insoluble precipitate in the reagent. Use of $Hg^{++}$ ion, on the other hand, would cause formation of an insoluble precipitate, and the complexing agent would in time be consumed as the precipitate is formed. Furthermore, formation of an insoluble precipitate would tend to remove dissolved organic matter from the sample by co-precipitation, thereby introducing an inaccuracy in the measurement of TOC in the sample.

Mercuric monohalide ion is formed by adding a quantity of mercuric halide and a quantity of mercuric nitrate $Hg(NO_3)_2$ to an aqueous solution containing nitric acid, with the molar concentration of the mercuric halide being at least equal to the molar concentration of the $Hg(NO_3)_2$ to insure that no free mercuric ion $Hg^{++}$ remains available for forming an insoluble precipitate. A slight excess of mercuric halide is recommended. The mercuric monohalide ion used according to this invention may be mercuric monochloride ion $HgCl^+$ or mercuric monobromide ion $HgBr^+$. To form $HgCl^{30}$, a quantity of mercuric chloride $HgCl_2$ is reacted with a quantity of $Hg(NO_3)_2$ according to the reaction $HgCl_2 + Hg(NO_3)_2 \rightarrow 2\ HgCl^+ + 2\ NO_3^-$. To form $HgBr^+$, a quantity of mercuric bromide $HgBr_2$ is reacted with a quantity of $Hg(NO_3)_2$ according to the reaction $HgBr_2 + Hg(NO_3)_2 \rightarrow 2\ HgBr^+ + 2\ NO_3^-$.

The oxidizing agent used according to this invention may be persulfate ion $S_2O_8^{--}$ or hydroxy free radical .OH. Persulfate ion is formed by adding a salt of persulfate, such as potassium persulfate $K_2S_2O_8$, sodium persulfate $Na_2S_2O_8$, or ammonium sulfate $(NH_4)S_2O_8$ to water. Hydroxy free radical is formed by dissociation of hydrogen peroxide $H_2O_2$ in water.

The reagent used in the practice of this invention is prepared by mixing an aqueous solution containing an oxidizing agent (e.g., $S_2O_8^{--}$ or .OH) with an aqueous solution containing mercuric monohalide ion (e.g., $HgCl^+$ or $HgBr^+$).

With a reagent according to the present invention, TOC analysis time for a typical seawater sample can be shortened to about four or five minutes, as compared to the eight minutes or longer required when the oxidizing reagent does not contain mercuric monohalide ion.

The invention is defined by the following claims and their equivalents.

What is claimed is:

1. A process for determining total organic carbon in an aqueous sample containing halide ion, said process comprising the steps of:
    (a) preparing an aqueous solution containing an oxidizing agent and mercuric monohalide ion without forming an insoluble precipitate;
    (b) introducing said sample into said solution;
    (c) irradiating said solution and said sample with electromagnetic energy to oxidize organic matter in said sample to carbon dioxide;
    (d) removing carbon dioxide produced by oxidation of said organic matter in said sample from said solution; and
    (e) measuring total carbon in said carbon dioxide.

2. The process of claim 1 wherein said aqueous solution is prepared by mixing said oxidizing agent with a solution containing mercuric monohalide ion, said solution containing mercuric monohalide ion being formed by adding a quantity of mercuric halide and a quantity of mercuric nitrate to an aqueous solution containing nitric acid, and molar concentration of said mercuric halide being at least equal to the molar concentration of said mercuric nitrate.

3. The process of claim 2 wherein said mercuric halide is mercuric chloride, and wherein said mercuric monohalide ion formed is mercuric monochloride ion.

4. The process of claim 2 wherein said mercuric halide is mercuric bromide, and wherein said mercuric monohalide ion formed is mercuric monobromide ion.

5. The process of claim 1 wherein said oxidizing agent contained in said aqueous solution is persulfate ion.

6. The process of claim 5 wherein said persulfate ion is formed by adding a salt of persulfate to water.

7. The process of claim 6 wherein said salt of persulfate is selected from the group consisting of potassium persulfate, sodium persulfate and ammonium persulfate.

8. The process of claim 1 wherein said oxidizing agent is formed by adding hydrogen peroxide to water.

9. The process of claim 1 wherein said irradiating electromagnetic energy has a frequency in a spectral range that includes ultraviolet and vacuum-ultraviolet light.

10. The process of claim 9 wherein said electromagnetic energy emanates from a mercury vapor lamp.

11. The process of claim 10 wherein said mercury vapor lamp is immersed in said aqueous solution containing said oxidizing agent.

12. The process of claim 1 wherein said carbon dioxide is removed from said aqueous solution by sparging said solution with a carbon-free gas.

13. The process of claim 12 wherein said sparging gas comprises a chemically inert gas.

14. The process of claim 13 wherein said inert gas is nitrogen.

15. The process of claim 12 wherein said sparging gas comprises oxygen.

16. The process of claim 1 wherein total carbon in said carbon dioxide is measured directly by coulometric titration.

17. The process of claim 1 wherein total carbon in said carbon dioxide is measured directly by a non-dispersive infrared detector.

18. The process of claim 1 wherein total carbon in said carbon dioxide is measured directly by conductometric means.

19. The process of claim 1 wherein total carbon in said carbon dioxide is measured by converting said carbon dioxide to methane, and by measuring total carbon in said methane.

20. The process of claim 19 wherein total carbon in said methane is measured by a flame ionization detector.

21. A reagent for use in the presence of ultraviolet radiation for oxidizing organic matter in an aqueous sample containing halide ion, said reagent containing an oxidizing agent and mercuric monohalide ion, said mercuric monohalide ion being produced by the process of adding a quantity of mercuric halide to a quantity of mercuric nitrate in an aqueous solution containing nitric acid, the molar concentration of said mercuric halide being at least equal to the molar concentration of said mercuric nitrate.

22. The reagent of claim 21 wherein said oxidizing agent comprises persulfate ion.

23. The reagent of claim 22 wherein said persulfate ion is produced by the process of adding a salt of persulfate to water.

24. The reagent of claim 23 wherein said salt of persulfate is selected from the group consisting of potassium persulfate, sodium persulfate and ammonium persulfate.

25. The reagent of claim 21 wherein said oxidizing agent comprises hydroxy free radical.

26. The reagent of claim 21 wherein said mercuric monohalide ion is mercuric monochloride ion, which is produced by adding a quantity of mercuric chloride to a quantity of mercuric nitrate in an aqueous solution containing nitric acid.

27. The reagent of claim 21 wherein said mercuric monohalide ion is mercuric monobromide ion, which is produced by adding a quantity of mercuric bromide to a quantity of mercuric nitrate in an aqueous solution containing nitric acid.

* * * * *